United States Patent [19]

Imondi

[11] Patent Number: 5,122,528
[45] Date of Patent: Jun. 16, 1992

[54] ANALGESIC USE OF BENZOBICYCLIC CARBOXAMIDES

[75] Inventor: Anthony R. Imondi, Westerville, Ohio

[73] Assignee: Erbamont, Inc., Dublin, Ohio

[21] Appl. No.: 681,183

[22] Filed: Apr. 5, 1991

Related U.S. Application Data

[63] Continuation-in-part of Ser. No. 614,773, Nov. 16, 1990, which is a continuation of Ser. No. 582,716, Sep. 14, 1990, which is a continuation of Ser. No. 402,952, Sep. 5, 1989, which is a continuation-in-part of Ser. No. 868,899, May 23, 1986, Pat. No. 4,888,353, which is a continuation-in-part of Ser. No. 835,006, Feb. 28, 1986, abandoned, which is a continuation-in-part of Ser. No. 564,641, Dec. 22, 1983, abandoned.

[51] Int. Cl.⁵ .............................................. A61K 31/44
[52] U.S. Cl. ................................................... 514/295
[58] Field of Search ......................................... 514/295

[56] References Cited

U.S. PATENT DOCUMENTS

| | | | |
|---|---|---|---|
| 4,797,406 | 1/1989 | Richardson et al. | 514/299 |
| 4,826,838 | 5/1989 | Richardson et al. | 514/210 |
| 4,857,517 | 8/1989 | Youssefyeh et al. | |
| 4,892,872 | 1/1990 | Tahara et al. | 415/230 |
| 4,920,219 | 4/1990 | Pelletier et al. | 540/523 |

FOREIGN PATENT DOCUMENTS

| | | |
|---|---|---|
| 0124783 | 11/1984 | European Pat. Off. |
| 0201165 | 11/1986 | European Pat. Off. |
| 0221702 | 5/1987 | European Pat. Off. |
| 0307172 | 7/1988 | European Pat. Off. |
| 0307172 | 7/1988 | European Pat. Off. |
| 1-104072 | 4/1989 | Japan . |
| WO8502847 | 7/1985 | PCT Int'l Appl. |

OTHER PUBLICATIONS

Medline Search "5HT₃ Antagonists and Analgesia" (1985–1991).

*Primary Examiner*—S. J. Friedman
*Attorney, Agent, or Firm*—Thompson, Hine and Flory

[57] ABSTRACT

Pyrrolidinyl derivatives of Benzofuran-7-carboximides with analgesic activity".

9 Claims, No Drawings

ANALGESIC USE OF BENZOBICYCLIC CARBOXAMIDES

CROSS-REFERENCE TO RELATED APPLICATION

This application is a continuation-in-part of U.S. application Ser. No. 07/614,733 filed Nov. 16, 1990 which, in turn, is a continuation of U.S. application Ser. No. 07/582,716 filed Sept. 14, 1990, which in turn is a continuation of U.S. application Ser. No. 402,952 filed Sept. 5, 1989, which in turn is a continuation-in-part of U.S. application Ser. No. 868,899 filed May 23, 1986 (now U.S. Pat. No. 4,888,353), which in turn is a continuation-in-part of U.S. application Ser. No. 835,006 filed Feb. 28, 1986 (now abandoned), which in turn is a continuation-in-part of U.S. application Ser. No. 564,641 filed Dec. 22, 1983 (now abandoned).

BACKGROUND

The present invention is based upon the discovery that benzofuran-7-carboxamides, and related compounds, and, more particularly, pyrrolidinyl derivatives thereof exhibit analgesic activity. Serotin (5-hydroxytryptamine), also known as 5HT, occurs endogenously in abundance in peripheral nerves and in blood platelets, and is known to cause pain in man through a specific action on 5HT receptors situated on terminals of primary afferent nerves. Compounds which antagonise the neuronal effects of 5HT have been shown to possess analgesic activity. In the periphery, (5-HT) has been shown to produce an algesic response as a component of the inflammatory process (Gupta and Bbide, Role of 5-HT in acute inflammation and anaphylaxis, Ind. J. Med. Res., 69, 651, 1979). Giordano & Dyche, Differential analgesic actions of serotonin 5-HT$_3$ receptor antagonists in the mouse, Neuropharmacology 28, 423, 1989; Giordano and Rogers, Peripherally administered serotonin 5-HT$_3$ receptor antagonists reduce inflammatory pain in rats, European J. Pharmacol., 170, 83, 1989 and Eschalier et al., Influence of a specific 5-HT$_3$ antagonist on carrageenan-induced hyperalgesia in rats, Pain 36, 249, 1989 have implicated a role for peripheral 5-HT$_3$ receptors in mediating this response. It has been proposed (see for example J. R. Fozard in Advances in Neurology Vol. 33, Raven Press New York 1982) to use compounds with serotonin antagonistic effects, i.e., 5-HT blocking effects, in the treatment of migraine. Particularly interesting are the compounds which antagonize the 5-HT$_3$ receptors. A particular active compound of this type is metoclopramide which J. B. Hughes in Med. J. Australia 2 No. 17. p. 580 (1977) has reported to lead to an immediate beneficial effect on a migraine attack on slow i.v. injection of 10 mg. 5HT also causes depolarisation of the rat isolated vagus nerve preparation through the same 5HT-receptor mechanism, and inhibition of this effect correlates with an analgesic effect in vivo.

SUMMARY OF THE INVENTION

The present invention is directed to a method for treating algesia or sensitivity to pain in a patient comprising administering to the patient an analgesic effective amount of a compound of formula I described below.

The present invention is more particularly directed to a method for treating algesia using benzofurancarboxamides or dihydrobenzofurancarboxamides of the formula (VIII) or (IX) below.

The invention is still more particularly directed to a method in which the moiety designated by A in formula (I), (VIII) or (IX) is a pyrrolidinyl group.

A more particular object of the invention is to provide a method for treating algesia using the compound 4-amino-5-chloro-N-pyrrolidinylmethyl-2,3-dihydrobenzo[b]furan-7-carboxamide (Compound 75) or pharmaceutically acceptable salt thereof.

A still more particular object of the invention is the use of the R-isomers of the foregoing compounds.

DETAILED DESCRIPTION OF THE INVENTION

The present invention is directed to a method for treating algesia comprising administering to a patient in need of such treatment an analgesic effective amount of a compound of formula (I):

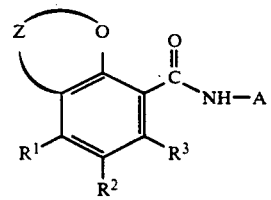

wherein Z represents the carbon and hydrogen atoms necessary to complete a substituted or unsubstituted, saturated or unsaturated, 5- to 7-membered ring; $R^1$, $R^2$, and $R^3$ may be the same or different and represent hydrogen, lower alkyl, cycloalkyl, lower alkoxy, amino, lower alkyl substituted amino, acylamido, sulfonamido, halogen or nitro group; provided that when Z represents the atoms necessary to complete a 2,3,4,5-tetrahydro-1-benzoxepin ring, $R^1$ may not equal hydrogen, amino or alkylamino and $R^2$ may not equal hydrogen or halogen; further provided that when Z represents the atoms necessary to complete a 2,2-dimethyl-2,3-dihydrobenzofuran ring, $R^1$, $R^2$ and $R^3$ may not simultaneously equal hydrogen, and when $R^2$ is flourine $R^1$ and $R^3$ may not equal hydrogen; still further provided that when Z represents the atoms necessary to complete a 2,2-dimethyl or a 2,2-diethyl 3,4-dihydrobenzopyran ring, $R^2$ may not equal fluorine or chlorine when $R^1$ and $R^3$ are hydrogen; A represents a group of the formula (II), (III), (IV), (V), (VI), or (VII).

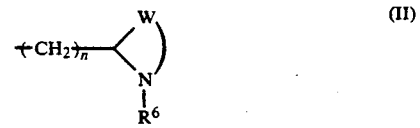 (II)

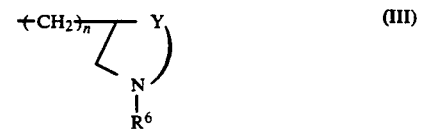 (III)

 (IV)

-continued

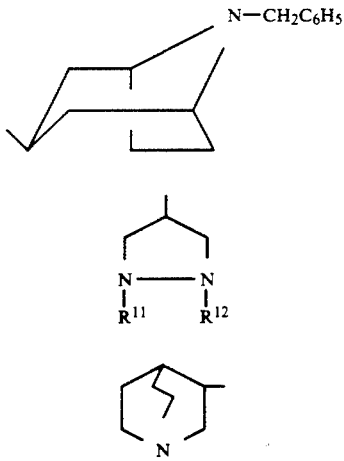
(V)

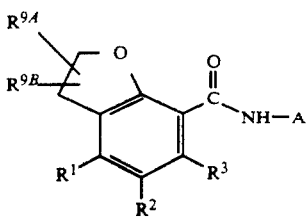
(IX)

(VI)

(VII)

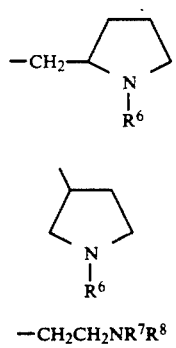

in which W represents a single bond or the carbon and hydrogen atoms necessary to complete a 3- to 8-membered saturated or an unsaturated ring; Y represents a single bond or the carbon and hydrogen atoms necessary to complete a 4- to 8-membered saturated or unsaturated ring; $R^6$ is hydrogen, lower alkyl, phenyl, phenalkyl, fluorine-substituted alkyl, propargyl, or allyl; $R^7$ and $R^8$ may be the same or different and are equal to hydrogen, lower alkyl, or lower hydroxyalkyl; $M^1$ and $M^2$ are the $R^{12}$ are the same or different and represent lower alkyl, cycloalkyl, or phenalkyl; n is 0 or an integer of 1 to 3.

In some preferred embodiments of the invention, A represents a group of the formulas (IIa), (IIIa), or (IVa):

(IIa)

—CH$_2$—⟨pyrrolidine-N-$R^6$⟩

(IIIa)

⟨pyrrolidine-N-$R^6$⟩

—CH$_2$CH$_2$NR$^7$R$^8$  (IVa)

wherein $R^6$, $R^7$ and $R^8$ are defined as in formula I above.

The present invention is more specifically directed to the analgesic use of benzo[b]furan and dihydrobenzo[b]furancarboxamides represented by the formulas (VIII) and (IX) wherein $R^1$, $R^2$, and $R^3$ are defined as above and $R^9$, $R^{9A}$, and $R^{9B}$ are selected from the group consisting of hydrogen, C1–3 alkyl or phenyl; and to pharmaceutical preparations containing these compounds as the active drug substance.

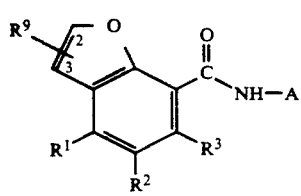
(VIII)

The present invention is still more specifically directed to the use of compounds of the formulas (I), (VIII), or (IX) wherein A is represented by the formula (IIa) and pharmaceutical compositions containing the same. Compounds are particularly preferred in which A is represented by the formula (IIa) and $R^1$ is amino, $R^2$ is chlorine, and $R^3$ is hydrogen. Still more preferably in formula (IIa), $R^6$ is hydrogen.

As described herein, the moiety, Z represents the atoms necessary to complete a 5- to 7-membered saturated or unsaturated oxygen containing ring for example, benzo[b]furan, dihydrobenzo[b]furan, benzoxepin, etc. In the preferred compounds Z forms a benzo[b]furan or a dihydrobenzo[b]furan ring which may be unsubstituted or monosubstituted or disubstituted in the 2- or 3-position by lower alkyl for example, methyl or ethyl; or phenyl. Where Z represents the atoms necessary to form a dihydrobenzo[b]furan ring, Z may be represented by the formula $C_nH_{2n}$ where n is 2 to 4 such as —CH$_2$CH$_2$—, —CH$_2$CH(CH$_3$)—, —C(CH$_3$)$_2$CH$_2$—, —CH$_2$C(CH$_3$)$_2$—, —CH(CH$_3$)CH$_2$—, —CH$_2$CH(C$_2$H$_5$)—, etc. Where Z represents the atoms necessary to form a benzofuran ring, Z may represent —CH=CH—, —CH=CCH$_3$—, or —CH$_3$C=CH—. Alternatively, Z may include a phenyl group at the 2- or 3-position.

The term "lower alkyl group" as used herein includes straight or branched chain alkyl groups of about 1 to 6 carbon atoms such as methyl, ethyl, propyl, i-propyl, n-butyl, t-butyl, amyl, isoamyl, n-hexyl, etc.

The term "lower alkoxy group" as used herein includes alkoxy groups which correspond to the aforementioned alkyl groups with the addition of the -O- linkage.

The term "phenyl group" and "phenalkyl group" as used herein include groups in which the phenyl moiety is unsubstituted or substituted by substituents such as methyl, ethyl, propyl, butyl, fluoro, chloro, bromo, iodo, amino, hydroxyl, methoxy, ethoxy, cyano, acetamido, sulfamoyl, and trifluoromethyl. Examples of phenalkyl groups include benzyl, phenethyl and phenylpropyl groups.

The term "cycloalkyl group" as used herein includes cycloalkyl groups containing up to 12 carbon atoms and preferably 4 to 8 carbon atoms such as cyclobutyl, cyclohexyl, cyclopentyl, ethylcyclohexyl.

Representative examples of the substituent groups represented by $R_1$, $R_2$, or $R_3$ include methyl, ethyl, n-propyl, i-propyl, and t-butyl groups.

Subject to the exclusions noted above, representative examples of the halogen atoms represented by $R^1$, $R^2$, and $R^3$ include fluorine, chlorine, bromine and iodine atoms.

The amino group represented by $R^1$, $R^2$, or $R^3$ may be an unsubstituted amino group or a substituted amino group of the formula —NR$^4$R$^5$ wherein R$^4$ and R$^5$ may be the same or different and selected from a hydrogen atom or a lower alkyl group. Otherwise, the amino group can be a substituted amino group such as an acylamido (e.g., acetamido) or a sulfonamido group of the formulae —NHCOR$^4$ and —NHSO$_2$R$^4$ wherein R$^4$ is defined as above.

Representative examples of the alkoxy groups for R$^1$, R$^2$, and R$^3$ include methoxy, ethoxy, and propoxy.

In the formula (II), W most preferably represents the atoms necessary to complete a pyrrolidinyl ring. A particularly advantageous compound is obtained when R$^6$ in formula (IIa) represents a hydrogen atom such that A is a 2-pyrrolidinylmethyl group. Otherwise, R$^6$ is preferably ethyl, benzyl, allyl, or propargyl.

In formula (III), Y may represent the atoms necessary to complete a 3-pyrrolidinyl ring, and R$^6$ may be benzyl.

In formula (IV), M$^1$ and M$^2$ are preferably hydrogen and R$^7$ and R$^8$ are both ethyl, both hydroxyethyl, or one of R$^7$ and R$^8$ is ethyl and the other hydroxyethyl.

In formula (VI), R$^{11}$ and R$^{12}$ may be the same or different and represent a methyl group, an ethyl group, an isopropyl group, a cyclobutyl group, a cyclopentyl group, a cyclohexyl group, and ethylcyclohexyl group, a benzyl group, or a phenpropyl group.

Compounds of particular usefulness are compounds in which A has the formula (IIa) and R$^1$, R$^2$, and R$^3$ are defined as follows:

| | | |
|---|---|---|
| R$^1$ = H | R$^2$ = Cl | R$^3$ = H |
| R$^1$ = H | R$^2$ = NH$_2$ | R$^3$ = H |
| R$^1$ = NH$_2$ | R$^2$ = Cl | R$^3$ = H |
| R$^1$ = H | R$^2$ = H | R$^3$ = OCH$_3$ |

The compounds of the invention may be used as the active drug substance in pharmaceutical compositions in the form of the free base, in the form of a salt, e.g., an acid addition salt, and as a hydrate. All forms are within the scope of this invention. Suitable addition salts are, for example, the maleate, hydrochloride, phosphate, fumarate, citrate, tartarate. Many of the compounds of the present invention contain an asymmetric carbon atom and have optical isomers. Compounds in which A is IIa appear to be more active as the R-isomer. Similarly, the amido group in some compounds have an endo or exo orientation one of which may be found to be more active than the other.

Representative examples of compounds in accordance with the present invention are shown in Table I. In some instances Table I designates a particular isomer, however, regardless of whether a particular isomer is designated or not, the invention includes the racemate as well as the isolated isomers.

TABLE

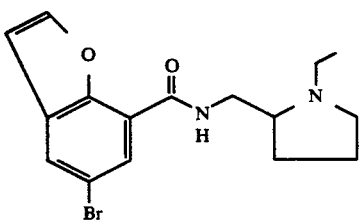
1.

TABLE-continued

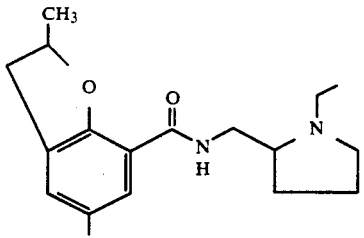
2.

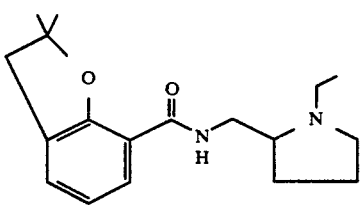
3.

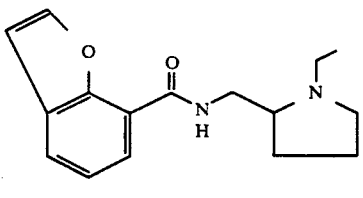
4.

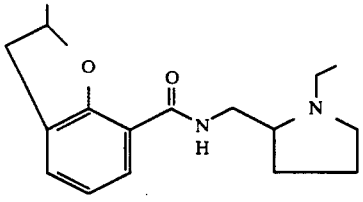
5.

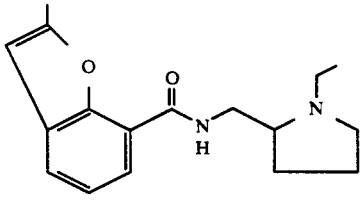
6.

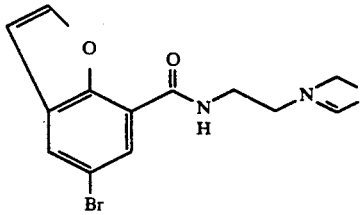
7.

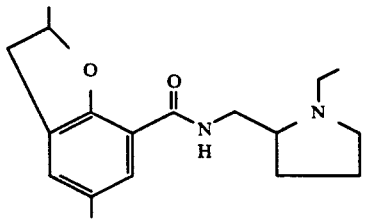
8.

TABLE-continued
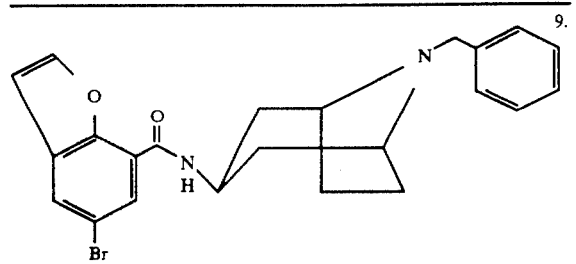  9.
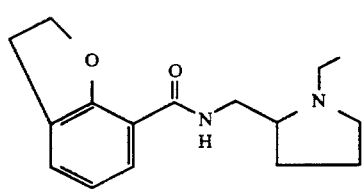  10.
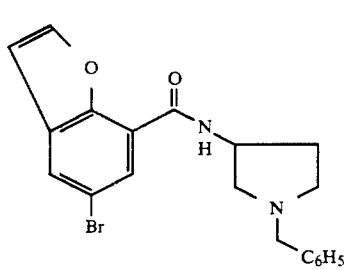  11.
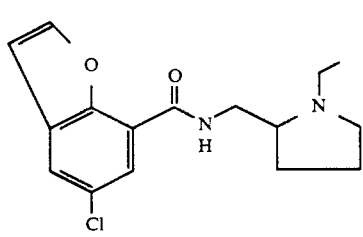  12.
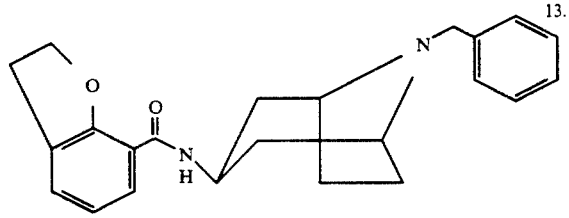  13.
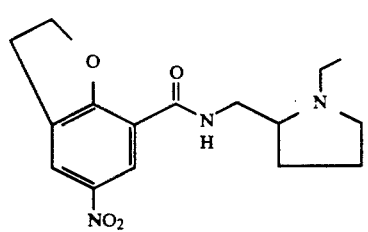  14.
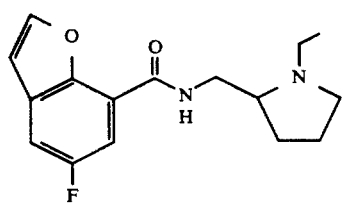  15.
TABLE-continued
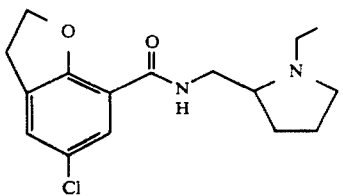  16.
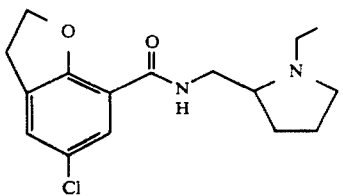  17.
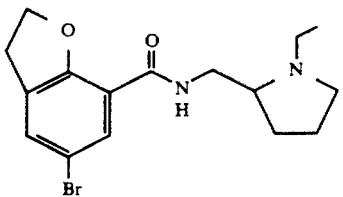  18.
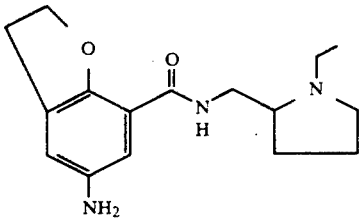  19.
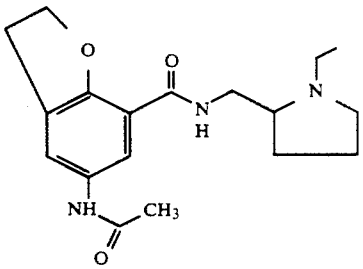  20.
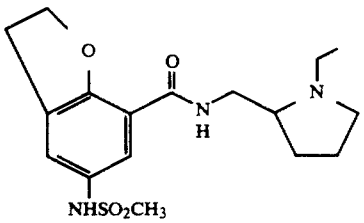  21.
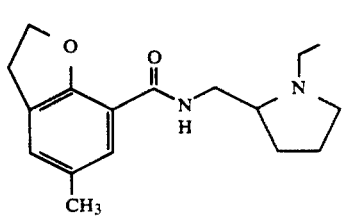  22.

TABLE-continued
23. 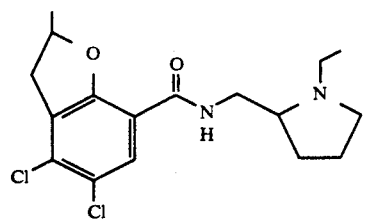
24. 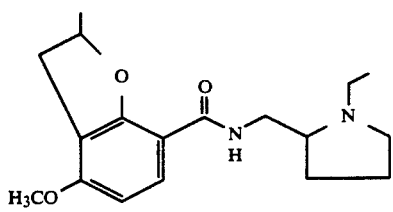
25. 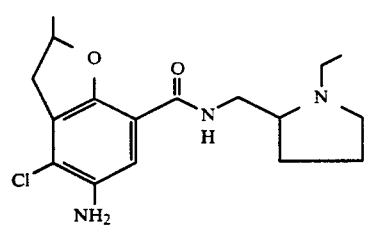
26. 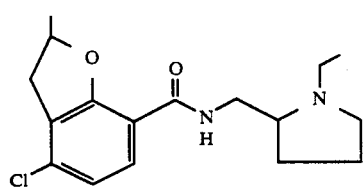
27. 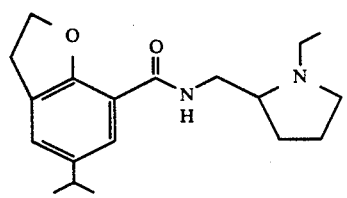
28. 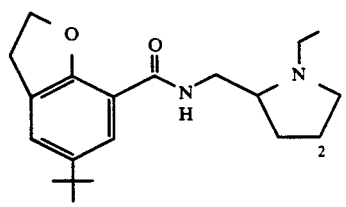
29. 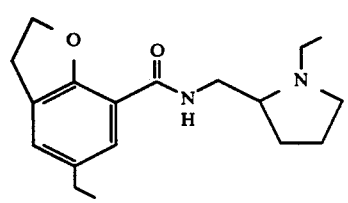
TABLE-continued
30. 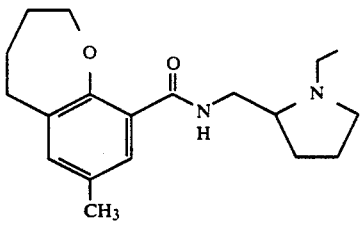
31. 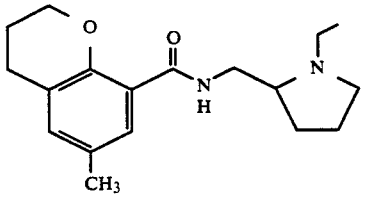
32. 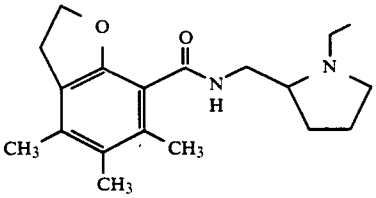
33. 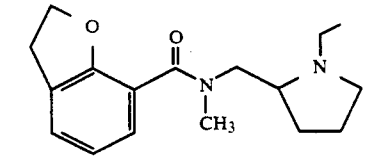
34. 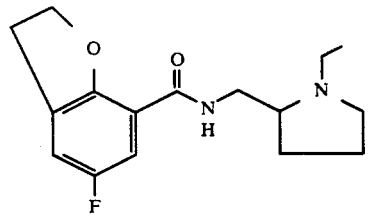
35. 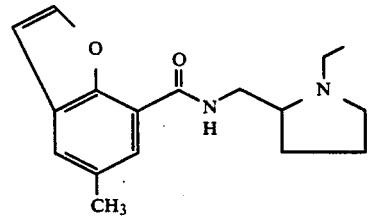
36. 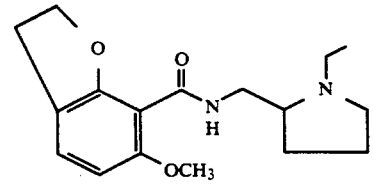

TABLE-continued
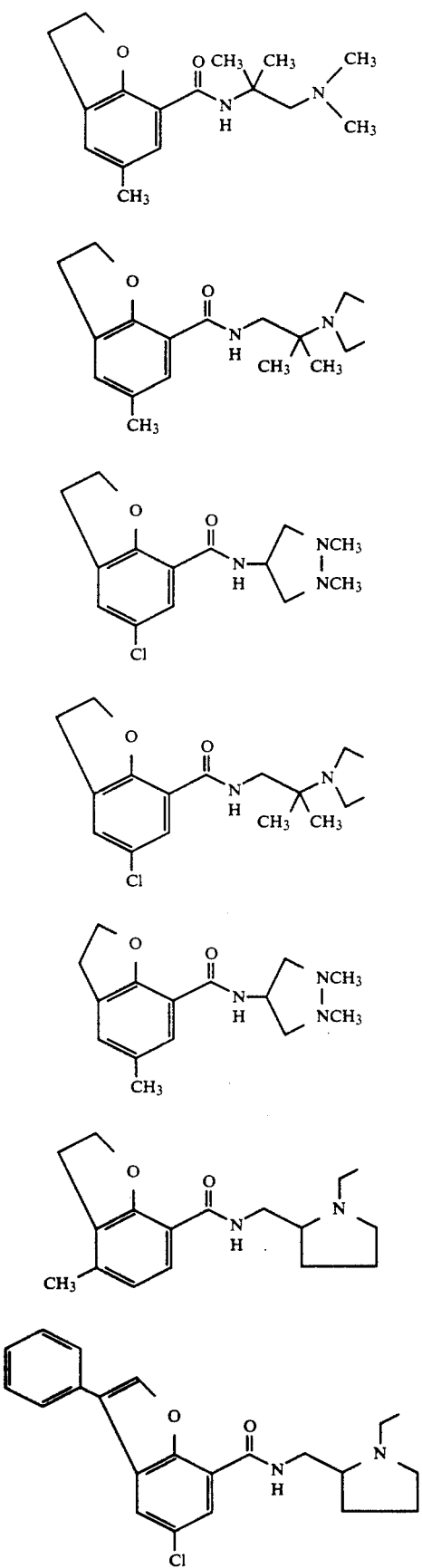
TABLE-continued
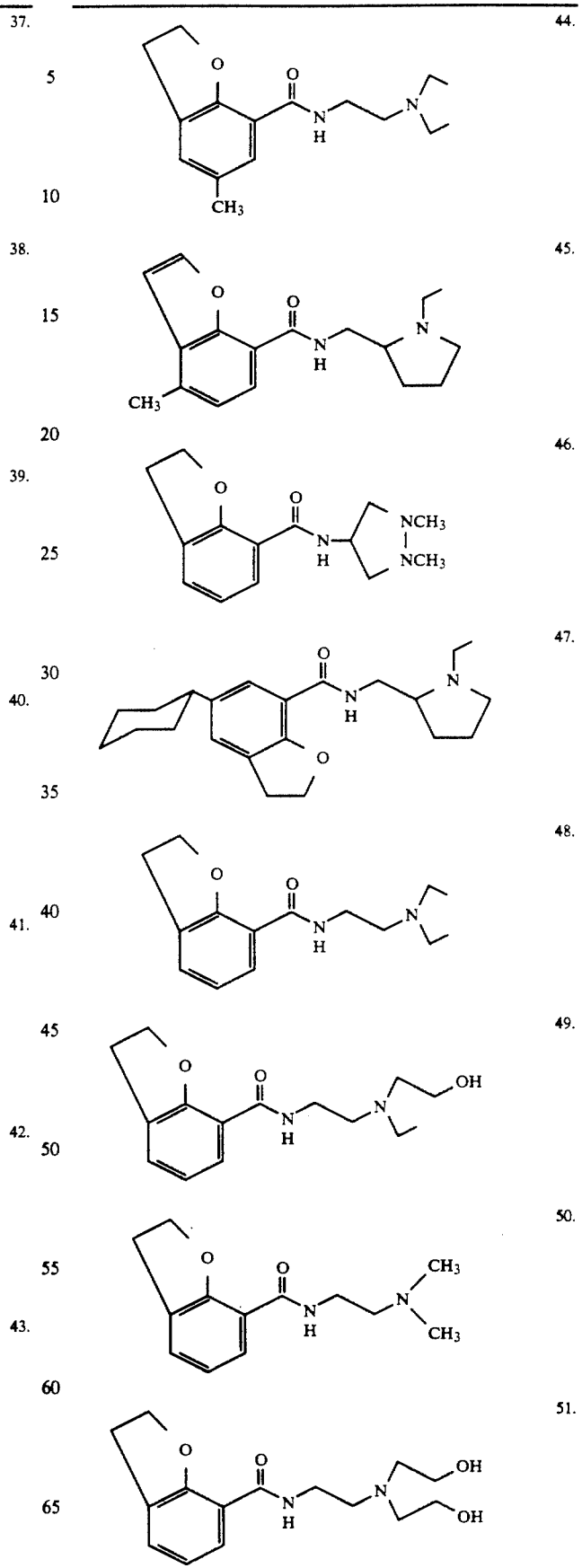

TABLE-continued
52. 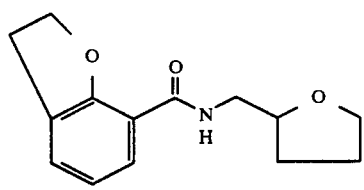
53. 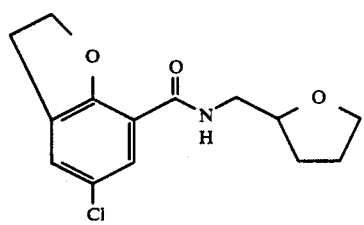
54. 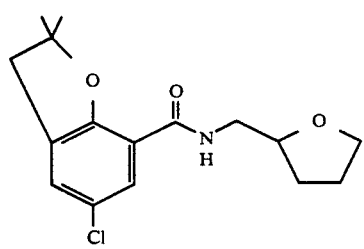
55. 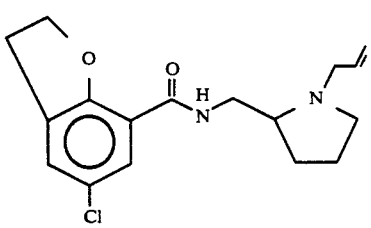
56. 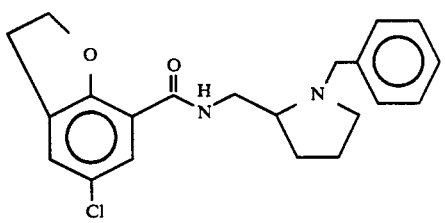
57. 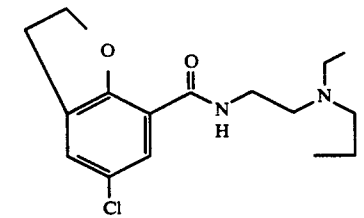
58. 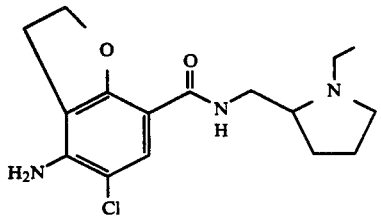
TABLE-continued
59. 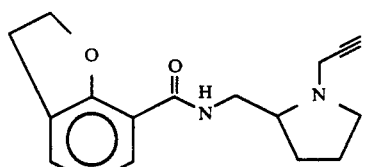
60. 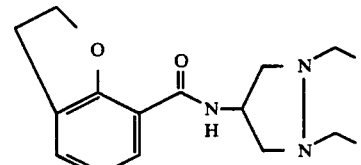
61. 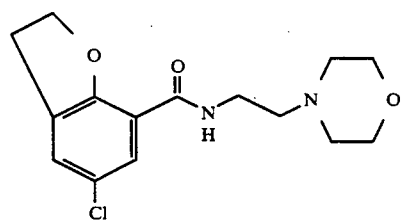
62. 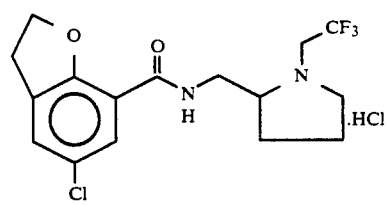
63. 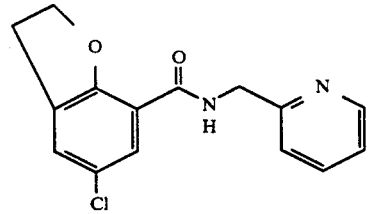
64. 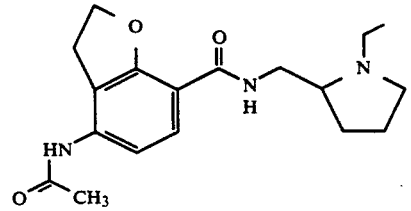
65. 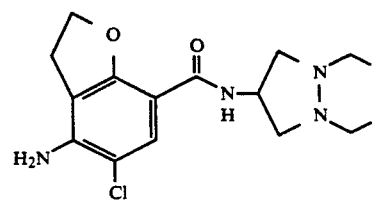

TABLE-continued
66. 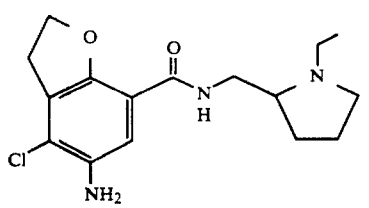
67. 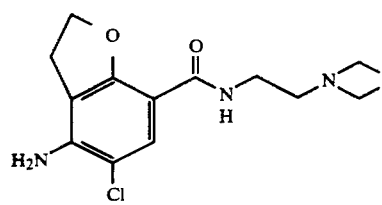
68. 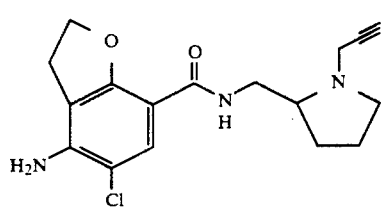
69. 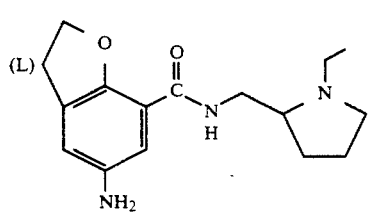
70. 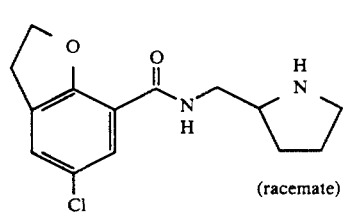
(racemate)
71. 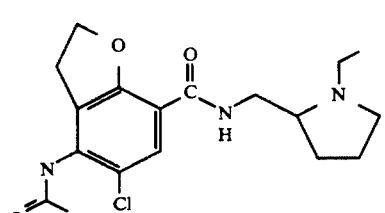
72. 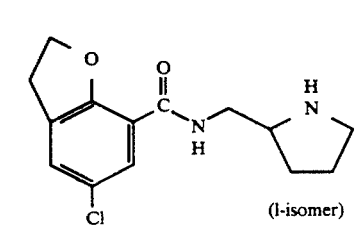
(l-isomer)
TABLE-continued
73. 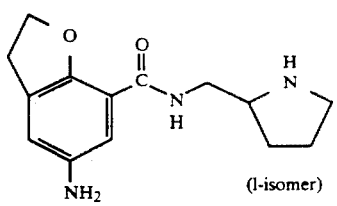
(l-isomer)
74. 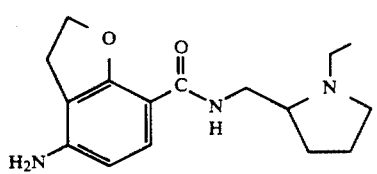
75. 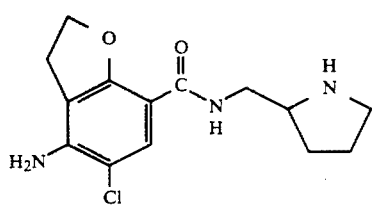
76. 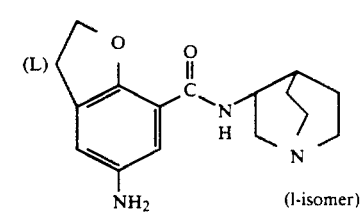
(l-isomer)
77. 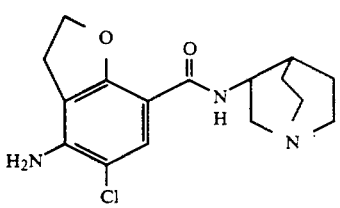
78. 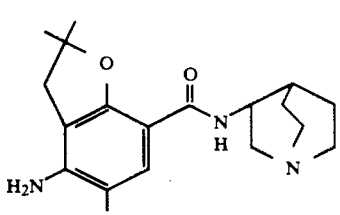
79. 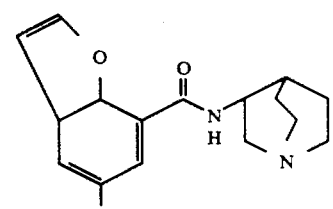

TABLE-continued
| 80. | 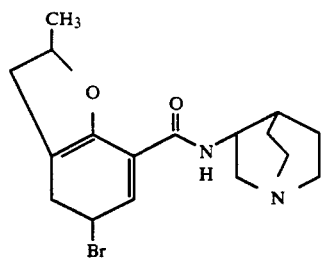 |
| --- | --- |
| 81. | 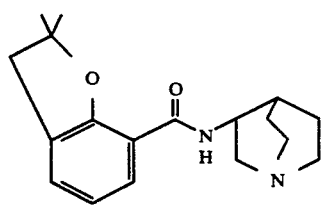 |
| 82. | 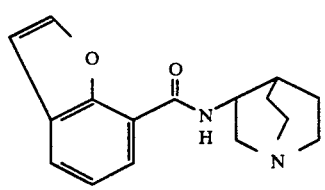 |
| 83. | 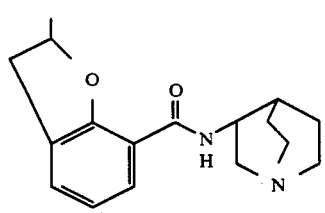 |
| 84. | 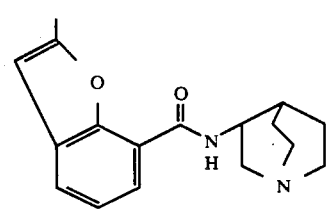 |
| 85. | 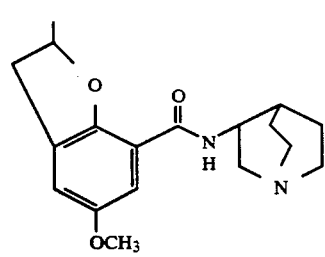 |
| 86. | 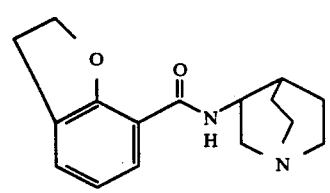 |
TABLE-continued
| 87. | 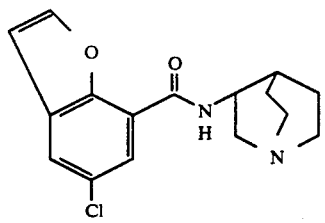 |
| --- | --- |
| 88. | 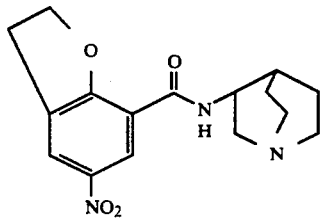 |
| 89. | 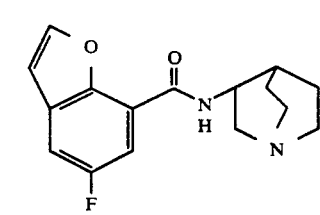 |
| 90. | 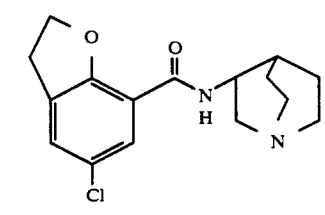 |
| 91. | 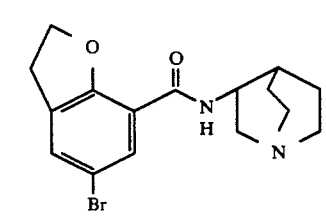 |
| 92. | 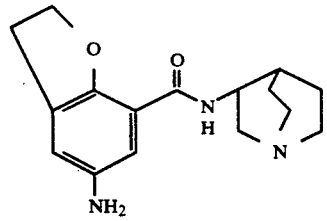 |
| 93. | 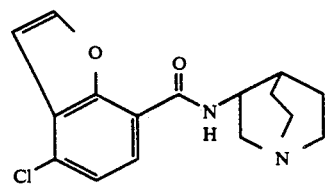 |

TABLE-continued
94. 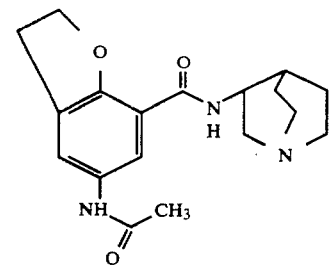
95. 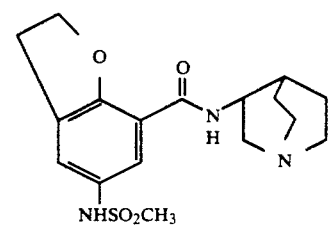
96. 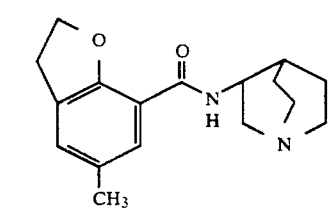
97. 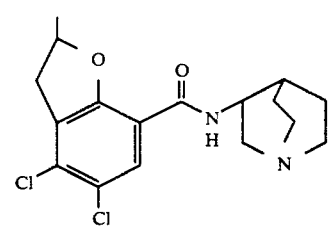
98. 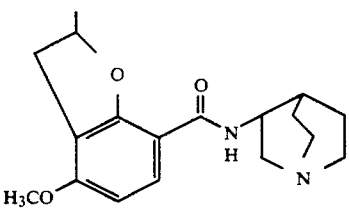
99. 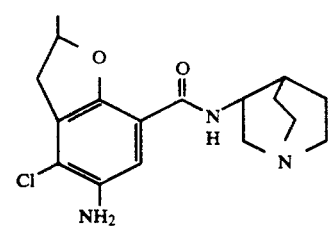
100. 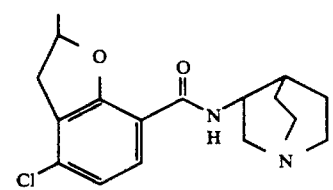
TABLE-continued
101. 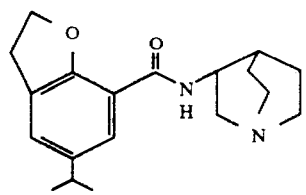
102. 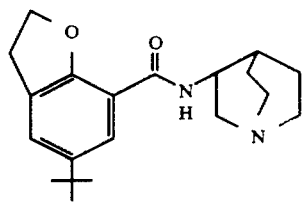
103. 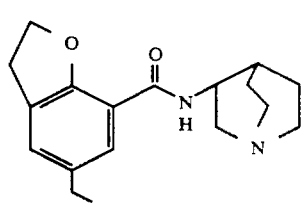
104. 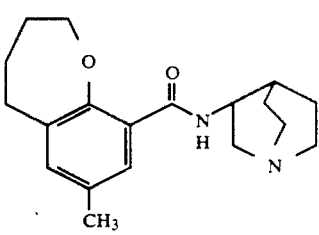
105. 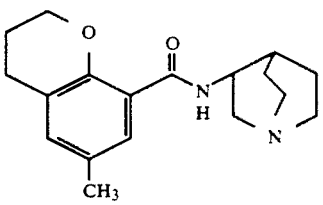
106. 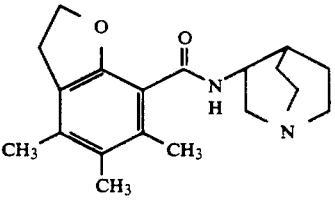
107. 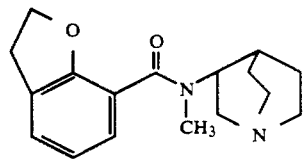

TABLE-continued
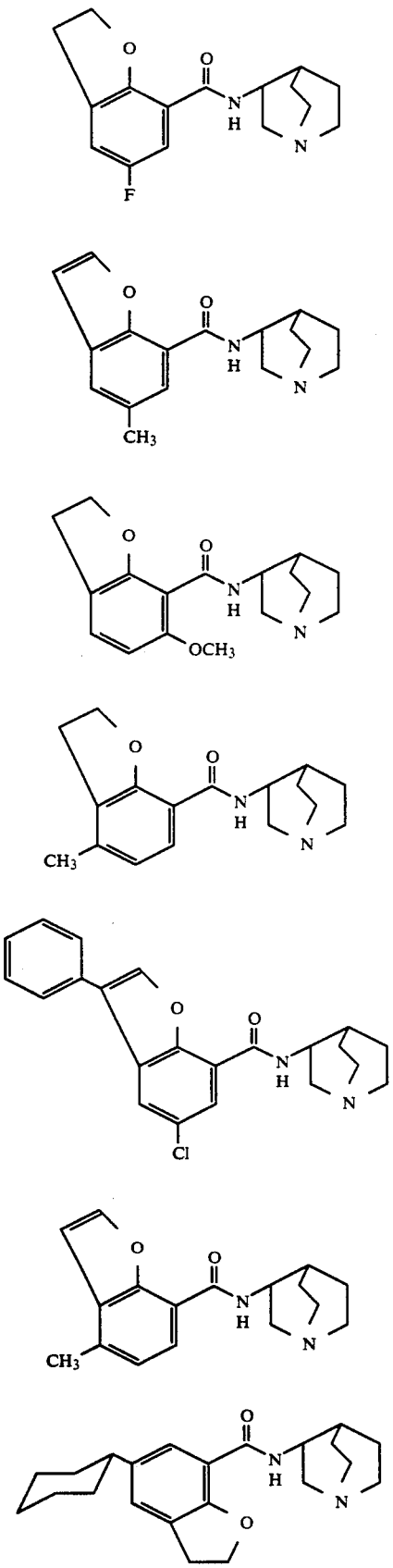
108.
109.
110.
111.
112.
113.
114.
TABLE-continued
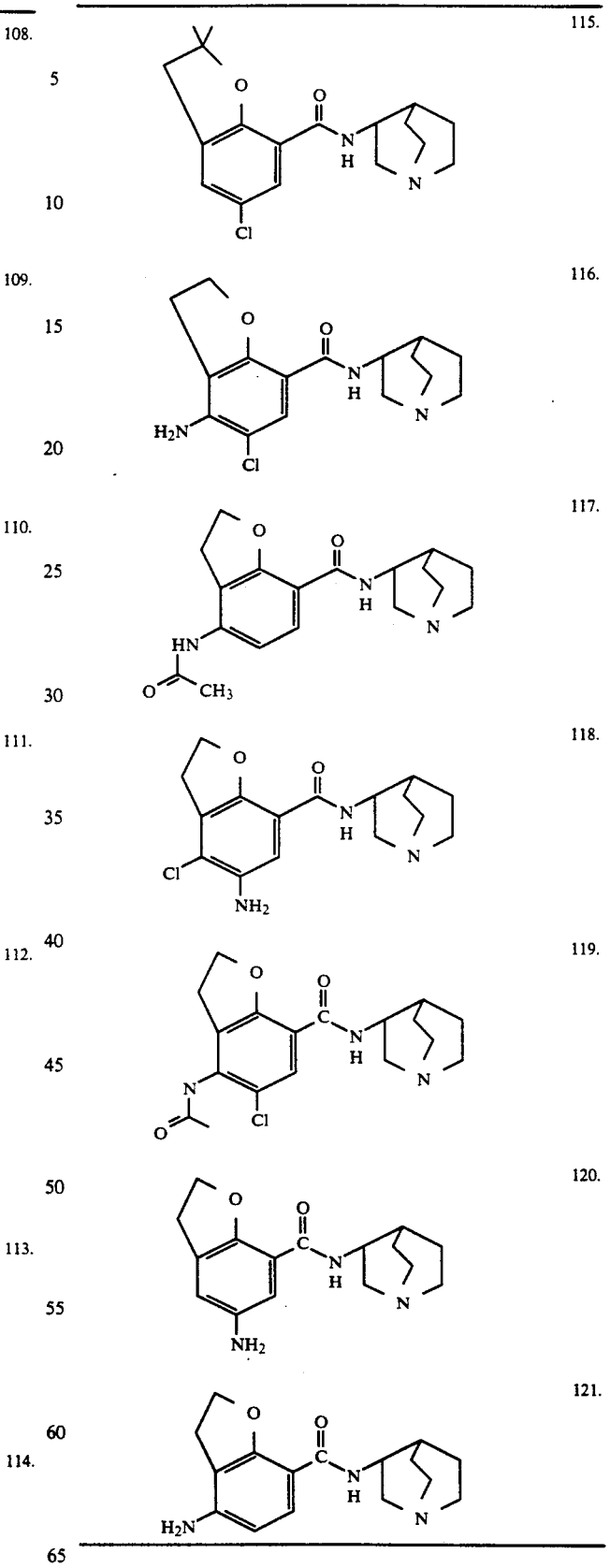
115.
116.
117.
118.
119.
120.
121.

Typically, the optically active isomers are prepared from the optically active amine which is condensed with the acid to produce the carboxamide.

The chemical syntheses of the analgesic compounds described herein are described in detail in U.S. Pat. No. 4,888,353 to Lednicer and U.S. Pat. No. 4,950,776 to Sun. In many instances, the compounds of the present invention can be prepared by condensing benzo[b]furan-7-carboxylic acid or dihydrobenzo[b]furan-7-carboxylic acid chlorides or esters with appropriate amines and recovering the carboxamides as acid salts. An alternative method of preparing the compounds utilizes an appropriately substituted benzofuran carboxylic acid which is reacted with ethyl chloroformate to form a mixed anhydride of the acid which is subsequently reacted with a solution of the amine (e.g., in dichloromethane). This method simplifies the synthesis where the carboxylic acid includes one or more substituents, such as an amino group, which is capable of reacting with the carboxyl group in competition with the amine. The synthesis of selected compounds is shown in the following examples.

EXAMPLE 1

Preparation of N-(1-azabicyclo[2.2.2]oct-3-yl)4-Amino-5—Chloro-2,3-Dihydrobenzo[b]Furan-7—Carboxamide, Compound No. 77

A suspension of 4-amino-7-carboxy-5-chloro-2,3-dihydrobenzofuran (16.02g 75 mmol.) and 1,1-carbonyldiimidazole (12.16 g. 75 mmol.) in 300 ml of tetrahydrofuran (THF) was stirred at room temperature under argon overnight. To this there was added 9.87 g (75.0 m mol.) of 3-aminoquinuclidine (available as the R or S isomer from Chiron Laboratory, Norway) available from Aldrich Chemical as the racemate) in 50 ml of THF. The mixture was stirred at room temperature for three hours and then refluxed overnight.

Thin layer chromatography showed the reaction was incomplete and another 0.5 g of 3-aminoquinuclidine was added. The mixture was refluxed for another hour. The solvent in the mixture was evaporated and the residue dissolved in 1N HCl(150 ml), washed with $CH_2Cl_2$ (2×100 ml). The aqueous layer was made alkaline with 2N NaOH and extracted with $CH_2Cl_2$ (3×200 ml). The organic layers were combined and were dried over anhydrous magnesium sulphate and evaporated to give 8.13 g of the free base.

To a methanol (50 ml) solution of the free base there was added 1.46 g of fumaric acid. The mixture was stirred for one (1) hour before ether (120 ml) was added and then left in the freezer overnight. The resulting precipitate was collected by filtration and dried to give 8.28 g of a white solid. M.W.=397.86, m.p.×216°-217° C.

As used herein, the phrase "active drug substance" (ADS) refers to the compounds described herein which are useful in the method of alleviating algesia or sensitivity to pain without loss of consciousness. The term "pharmaceutical dosage form" as used herein refers to the "finished" or formulated dosage form which comprises the active drug substance as well as pharmaceutically acceptable carriers, diluents, adjuvants and the like.

The active drug substance described herein may be administered orally or parenterally. Suitable pharmaceutically acceptable diluents, carriers, or adjuvants known in the art may be used to prepare analgesic compositions such diluents, carriers, etc. are generally a solid or liquid or a mixture of a solid and a liquid.

Solid form compositions or pharmaceutical dosage forms suitable for use herein include powders, granules, tablets, capsules (e.g. hard and soft gelatin capsules) filled with powders, granules, or in the case of a soft gelatin capsule, a liquid, suppositories and pessaries. A solid carrier can be, for example, one or more substances which may also act as a lubricant, solubiliser, suspending agent, filler, glidant, compression aid, binder or tablet-disintegrating agent, it can also be an encapsulating material. In powders, the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferable 1 to 80% of the active ingredient. Suitable solid carriers include, for example, calcium phosphate, magnesium stearate, talc, sugars, lactose, dextrin, starch, gelatin, cullulose, methyl cellulose, sodium carboxymethyl cellulose, polyvinylpyrrolidine, low melting waxes and ion exchange resins.

Liquid form compositions include, for example, solutions, suspensions, emulsions, syrups, elixirs and pressurized compositions. The active ingredients, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile parenteral solutions may be administered intravenously. When the active drug substance is administered intravenously (I.V.), most often the pharmaceutical dosage form will be a sterile lyophilizate which is reconstituted with a sterile pharmaceutical diluent prior to I.V. administration to the patient.

The compounds discussed herein have 5-$HT_3$ antagonism and are considered to be useful in treating inflammatory pain as is associated with headaches, migraines and cluster headaches as well as painful discomforts associated with cold, flu, muscular aches, sprains, and arthritis.

As used herein, the term "analgesically effective amount" refers to the concentration of the active drug substance in a pharmaceutically acceptable as well as biologically acceptable pharmaceutical dosage form effective to reduce or alleviate inflammatory pain in a patient suffering from such condition. Such amount will vary from patient to patient depending on such factors as body weight, age, overall general health as well as a consideration of any other medications being administered to the patient at the same time.

In general, from about 1.0 mg to about 10.0 mg per kilogram body weight will be effective to control or alleviate inflammatory pain. As would be recognized by the skilled physician or pharmacist, in elderly and debilitated patients, the dosage should be limited to the smallest effective amount. The term "inflammatory pain" or "inflammatory pain disorder" as used herein refers to a condition which is characterized by a feeling of inflammatory pain associated with migraines or cluster headaches.

Example 2 illustrates the use of the compounds described herein in tests which have been found to be predictive of inflammatory pain.

EXAMPLE 2

Methods

Male Sprague-Dawley rats (200-300 g.) were used in all experiments. Animals were housed in standard 360 cm2 cages, two per cage, and were maintained on a 12 hr. light/dark cycle under conditions of constant 23° C. ambient temperature, and were allowed food, water and conspecific contact ad libitum prior to experimental use. Separate animals were used at each dose of S and R isomers of Compounds Nos. 75 and 77. Each animal was used only once.

Pure S or R isomers of Compound No. 75 (4-amino-5-chloro-N-[2-pyrrolidylmethyl]-2,3-dihydrobenzo[b]furan-7-carboxamide) and Compound No. 77 (4-amino-N-[1-azabicyclo(2,2,2) oct-3-yl]5-chloro-2,3-dihydrobenzo[b]furan-7-carboxamide) were freshly prepared in sterile saline, pH 7.0, immediately prior to each experimental session. Drugs were subcutaneously injected in a total volume of 1 cc/kg total body weight. Drug doses and temporal parameters of injection-test intervals were determined in pilot studies.

All nociceptive tests were conducted 30 minutes following subcutaneous (s.c.) administration of S or R isomers of Compounds Nos. 75 or 77 (0.1-10 mg/kg); control animals received s.c. injections of saline vehicle alone. Acute thermal nociception was assessed using the hot-plate test in which each animal was placed upon a hot-plate (54° C.) and the time-latency required to elicit licking and/or lifting of the paws was recorded. Mechanical nociception was tested according to the method of Giordano and Barr (1987). In this paradigm, a blunt probe, 0.2 cm in diameter, was applied at a dynometric force of 20 g. to the dorsal side of the forepaw, and withdrawal response latencies were recorded. To test chemical inflammatory nociception, the formalin test described by Dubuisson and Dennis (1977) was used: 50 ul of 1.0% formalin solution was injected into the plantar surface of the right or left hindpaw. Algesic responses of lifting, licking and attending the affected limb were recorded for 5 minutes after formalin delivery.

Additionally, animals were assessed for changes in ability of limb flexion/withdrawal, righting reflex, arousal/sedation, grooming, rearing, respiration and conspecific interaction at each dose of S and R isomers of Compounds Nos. 75 and 77.

Data were statistically analyzed using analysis of variance (ANOVA) and power-adjusted Student's t-test. Significance was indicated at the level of $P \leq 0.05$.

Neither isomer of Compounds Nos. 75 or 77 produced changes in motor performance, respiration, level of arousal or overt behavioral activity (i.e., grooming, rearing, contact) at any dose tested. Neither isomer of Compound 77 produced statistically significant analgesia in the acute thermal pain test. As well, neither S or R form of Compound No. 77 was analgesic against acute mechanical or formalin-induced inflammatory nociception. Similarly, neither S or R isomer of Compound No. 75 produced analgesia against acute thermal or mechanical pain. However, in the formalin test of acute inflammatory-pain, the R isomer of Compound No. 75 produced significant analgesic effects at 3 mg/kg and 10 mg/kg doses ($P<0.05$) that were statistically equivalent. In contrast, the S isomer of Compound No. 75 produced analgesia only at 1 mg/kg dose ($P<0.05$).

The lack of effect of Compound Nos. 75 and 77 in acute thermal and mechanical inflammatory pain tests suggests that 5-$HT_3$ receptors are not involved with transmission of nociceptive signals within these stimulus modalities. The efficacy of R and S isomers of Compound 75 against formalin-induced inflammatory pain is consistent with previous studies suggesting that peripheral 5-$HT_3$ receptors mediate the algesic response to inflammation.

There are several possible explanations for the differential analgesic action of Compound Nos. 75 and 77 in the formalin test. First, it may be that these agents exert distinct activity at (peripheral) 5-$HT_3$ receptors involved in inflammatory nociception. This is unlikely given the relative equivalence of these compounds in in vitro 5-$HT_3$ receptor assays. Second, the structural distinctions between these agents may affect their extravascular access to tissue and peripheral neural compartments at which 5-$HT_3$ receptor-mediated activity occurs. Third, it is also possible that structural dissimilarities may induce differential metabolism of Compounds Nos. 75 and 77. Such metabolic effects might alter both tissue access (i.e., bioavailability) as well as potency at the 5-$HT_3$ receptors.

Although 5-$HT_3$ receptors have been localized to both the peripheral and central nociceptive neuraxes, these systems seem to function oppositionally. In light of such findings, it is likely that the analgesic action of Compound No. 75 in the formalin test reflects pharmacologic action at peripheral, but not central 5-$HT_3$ receptors involved in inflammatory nociception. Given the complexity of the inflammatory process, these substrates may be neural, vascular, or both.

While the present invention has been described in detail and by reference to specific embodiments thereof, it will be recognized that numerous modifications and variations are possible without departing from the scope of the invention as defined by the following claims.

What is claimed is:

1. A method for the treatment of algesia comprising orally or parenterally administering to a patient in need of such treatment an analgesic effective amount of a compound of the formula (I) or a pharmaceutically acceptable salt thereof.

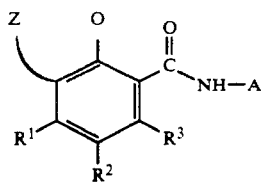

wherein Z represents the carbon and hydrogen atoms necessary to complete a substituted or unsubstituted, saturated or unsaturated, 5- to 7-membered ring; $R^1$, $R^2$ and $R^3$ may be the same or different and represent a member selected from the group consisting of hydrogen, lower alkyl, cycloalkyl, lower alkoxy, amino, lower alkyl substituted amino, acylamido, sulfamido, halogen and nitro; A represents a moiety selected from the group consisting of formulas:

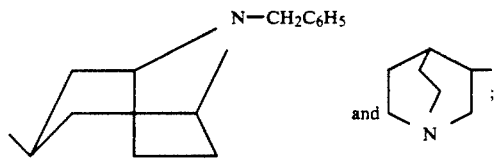

provided that when Z represents the atoms necessary to complete a 2,3,4,5-tetrahydro-1-benzoxepin ring, $R^1$ may not equal hydrogen, amino, or alkylamino and $R^2$ may not equal hydrogen or halogen; when Z represents the atoms necessary to complete a 2,2-dimethyl-2,3-dihydrobenofuran ring, $R^1$, $R^2$ and $R^3$ may not simultaneously equal hydrogen and when $R^2$ is fluorine, $R^1$ and $R^3$ may not equal hydrogen; and when Z represents the atoms necessary to complete a 2,2-dimethyl or a 2,2-diethyl, 3,4-dihydrobenzopyran ring, $R^2$ may not equal fluorine or chlorine when $R^1$ and $R^3$ are hydrogen; provided that when Z represents the atoms necessary to complete a 2,3,4,5-tetrahydro-1-benzoxepin ring, $R^1$ may not equal hydrogen amino, or alkylamino and $R^2$ may not equal hydrogen or halogen; when Z represents the atoms necessary to complete a 2,2-dimethyl-2,3-dihydrobenzofuran ring, $R^1$, $R^2$ and $R^3$ may not simultaneously equal hydrogen and when $R^2$ is fluorine, $R^1$ and $R^3$ may not equal hydrogen; and when Z represents the atoms necessary to complete a 2,2-dimethyl or a 2,2-diethyl 3,4-dihydrobenzopyran ring, $R^2$ may not equal fluorine or chlorine when $R^1$ and $R_3$ are hydrogen.

2. The method of claim 1 wherein Z represents the atoms necessary to complete an unsubstituted dihydrofuran ring.

3. The method of claim 1 wherein one of $R^1$ and $R^2$ is amino.

4. The method of claim 1 wherein $R^1$ is amino, $R^2$ is chloro and $R^3$ is hydrogen.

5. The method of claim 1 wherein $R^1$ is amino, $R^2$ is chloro and $R^3$ is hydrogen.

6. The method of claim 1 wherein said compound is represented by the formula VIII

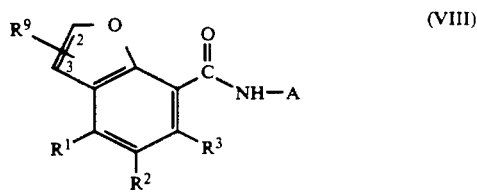

where A, $R^1$, $R^2$ and $R^3$ are defined as in claim 1 and $R^9$ is hydrogen, lower alkyl, cycloalkyl or phenyl.

7. The method of claim 1 wherein said compound is represented by the formula (IX)

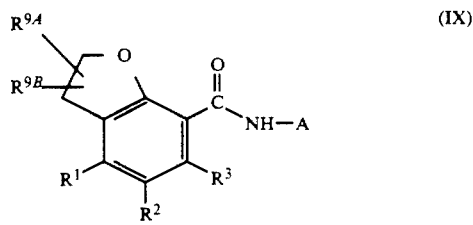

where A, $R^1$, $R^2$ and $R^3$ are defined as in claim 1 and $R^9A$ and $R^9B$ are independently hydrogen, lower alkyl, cycloalkyl or phenyl.

8. The method of claim 4 wherein said compound has the R-isomer configuration.

9. The method of claim 5 wherein said compound has the R-isomer configuration.

* * * * *

UNITED STATES PATENT AND TRADEMARK OFFICE
CERTIFICATE OF CORRECTION

PATENT NO.   : 5,122,528
DATED        : June 16, 1992
INVENTOR(S)  : Anthony R. Imondi It is certified that error appears in the above-indentified patent and that said Letters Patent is hereby corrected as shown below:

Column 27, line 3, in formula (1), insert a line from "Z" to "O" (first occurrence).

Column 27, line 42, insert —,— between the words "hydrogen" and "amino".

Signed and Sealed this

Thirty-first Day of August, 1993

Attest:

BRUCE LEHMAN

*Attesting Officer*     Commissioner of Patents and Trademarks